United States Patent [19]

Umio et al.

[11] Patent Number: 4,879,301

[45] Date of Patent: Nov. 7, 1989

[54] ANTIALLERGIC AND ANTIINFLAMMATORY BENZOTHIAZOLINONE DERIVATIVES

[75] Inventors: Suminori Umio, Kawanishi; Shizuo Kozasa, Suita; Takahiro Yabuuchi, Takarazuka, all of Japan

[73] Assignees: Hoei Pharmaceutical Co., Ltd., Osaka; Research Institute for Production Developement, Kyoto, both of Japan

[21] Appl. No.: 186,439

[22] Filed: Apr. 26, 1988

[30] Foreign Application Priority Data

Apr. 28, 1987 [JP] Japan .................................. 62-106961
Feb. 1, 1988 [JP] Japan .................................... 63-21754

[51] Int. Cl.$^4$ .................... A61K 31/445; C07D 417/06
[52] U.S. Cl. ...................................... 514/321; 546/198
[58] Field of Search ......................... 546/198; 514/321

[56] References Cited

U.S. PATENT DOCUMENTS 3,755,327 8/1973 Umio .................................... 544/368

OTHER PUBLICATIONS

Chemical Abstracts, 92:94383b(1980)[JPN. Kokai 79 92,956, 7/23/79, Veda].

Primary Examiner—Richard A. Schwartz
Attorney, Agent, or Firm—Bryan, Cave, McPheeters & McRoberts

[57] ABSTRACT

Benzothiazolone Derivatives represented by the formula:

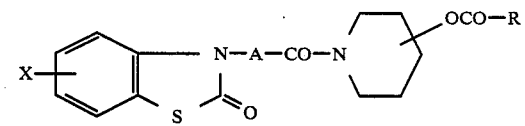

in which X is halogen, A is alkylene and R is alkoxy, amino, substituted amino, carboxyalkyl or carboxyalkylene, which are useful as antiallergic or antiinflammatory agents.

4 Claims, No Drawings

ANTIALLERGIC AND ANTIINFLAMMATORY BENZOTHIAZOLINONE DERIVATIVES

BACKGROUND OF THE INVENTION

1. Field of the Invention

This invention relates to novel benzothiazolinone derivatives, their production and pharmaceutical composition. The compounds of the invention are useful as anti-allergic or anti-inflammatory agents.

2. Description of the Prior Art

Certain 3-substituted-carbonyl(lower)alkyl-2-benzothiazolinones such as 5-chloro-3-(4-hydroxypiperidinocarbonylmethyl)benzothiazoline-2-one are known as anti-allergic agents (see U.S. Pat. No. 3,755,327).

SUMMARY OF THE INVENTION

This invention provides a benzothiazolinone derivative of the formula (I):

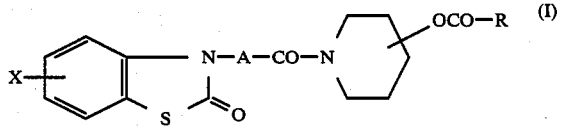

in which A is a lower alkylene group; X is a halogen atom, R is the group $-OR^1$, $-NR^2R^3$ or $-R^4-COOH$ wherein $R^1$ is a lower alkyl group, $R^2$ and $R^3$ are hydrogen atom or a lower alkyl group and $R^4$ is a lower alkylene or alkenylene group, and pharmaceutically acceptable salt thereof.

The invention also provides the production and phamaceutical composition of the above mentioned compounds.

DESCRIPTION OF THE PREFERRED EMBODIMENTS

In the above formula (I), the lower alkylene group for the symbols A and $R^4$ means a straight chain or branched chain alkylene group containing 1 to 6 carbon atoms, such as methylene, propylene, trimethylene, tetramethylene, pentamethylene or hexamethylene. The lower alkenylene group for the symbol $R^4$ means a straight chain or branched chain alkenylene group containing 2 to 6 carbon atoms, such as vinylene, propenylene, butenylene, pentenylene, hexenylene or 2-methyl-3-butenylene. The lower alkyl group for the symbols $R^1$, $R^2$ and $R^3$ means a straight chain or branched chain alkyl group containing 1 to 6 carbon atoms, such as methyl, ethyl, propyl, butyl, pentyl, hexyl, isopropyl, isobutyl or tertiary butyl. The halogen atom for the symbol X may be fluorine, chlorine, bromine or iodine atom.

A preferred alkylene group is methylene group and a preferred halogen atom is chlorine atom which can exist at the 4, 5, 6 or 7th position of the benzothiazoline ring. Preferred examples of the group $-OCO-R$ in the formula (I) are ethoxycarbonyloxy, N-methylcarbamoyloxy, N-ethylcarbamoyloxy N,N-dimethylcarbamoyloxy, carbamoyloxy, carboxyethylcarbonyloxy and carboxyvinylcarbonyloxy, which are preferred to be at the 3 or 4th position of the piperidine ring.

Examples of the pharmaceutically acceptable salts of the benzothiazolinone derivatives (I) include alkali metal salts such as sodium salt and potassium salt, alkaline earth metal salts such as calcium salt and magnesium salt and ammonium salt.

The benzothiazoline derivatives (I) can be prepared by the following methods.

Preparation method 1:

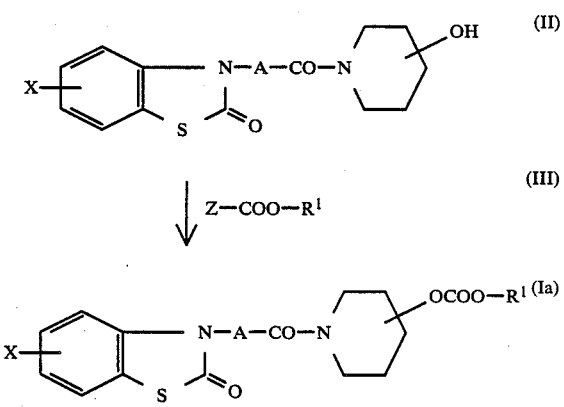

Preparation method 2:

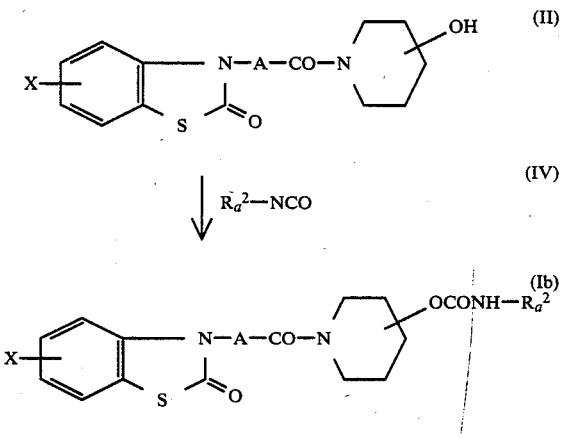

Preparation method 3:

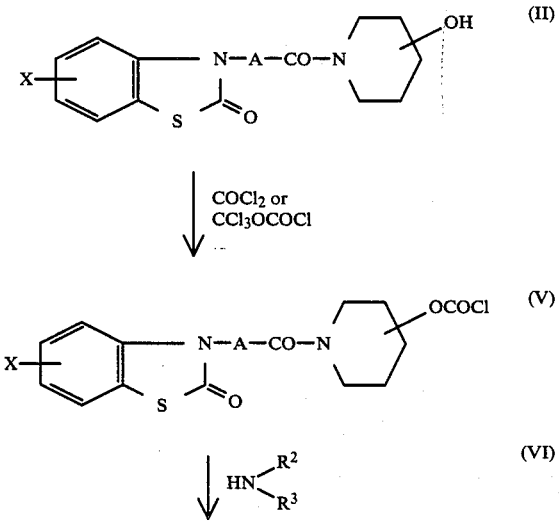

-continued

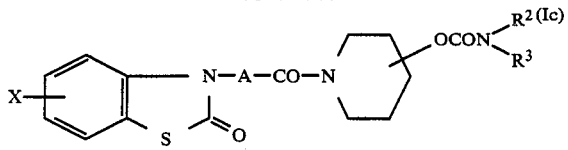

Preparation method 4:

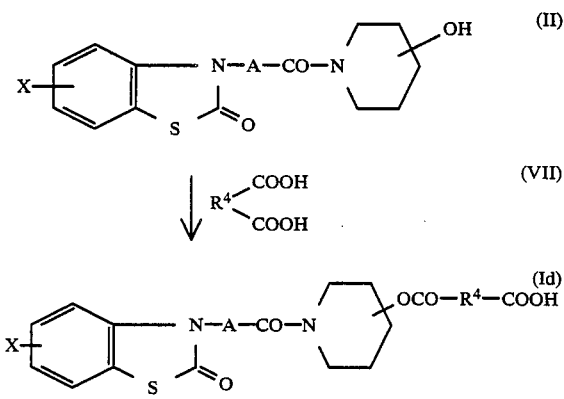

In the above reaction formulae, the symbols A, X, $R^1$, $R^2$, $R^3$ and $R^4$ have the same meanings as defined above, $Ra^2$ is a lower alkyl group and Z is a halogen atom.

Details of the above mentioned methods are as follows.

Preparation method 1:

The benzothiazolinone derivatives (Ia) can be prepared by reacting the starting compound (II) or its salt with the starting compound (III).

The compound (II) can be prepared by the method disclosed in U.S. Pat. No. 3,755,327.

Examples of the salts of the starting compound (II) include alkali metal salts such as sodium salt, potassium salt and lithium salt.

Examples of the halogen atoms for Z of the starting compounds (III) include the same atoms as defined above.

This reaction can be generally carried out in a solvent such as pyridine, dimethylaniline, trimethylamine, dioxane, tetrahydrofuran or N,N-dimethylformamide with warming or heating.

Preparation method 2:

The benzothiazolinone derivatives (Ib) can be prepared by reacting the starting compound (II) or its salt with the starting compound (IV).

This reaction can be generally carried out in a solvent such as pyridine, tetrahydrofuran, dioxane or N,N-dimethylformamide with warming or heating.

Preparation method 3:

The benzothiazolinone derivative (Ic) can be prepared by reacting the starting compound (II) or its salt with phosgene or trichloromethylchloroformate to obtain the intermediate (V), followed by the reaction with the starting compound (VI) or its salt.

Examples of the salts of the starting compound (VI) include salts with inorganic acids such as hydrochloric acid, nitric acid and sulphuric acid.

The first stage in the above reactions can be generally carried out in a solvent such as dioxane, tetrahydrofuran or N,N-dimethylformamide with warming or heating.

The second stage can be also generally carried out in a solvent such as dioxane, tetrahydrofuran or N,N-dimethylformamide with warming or heating. When the salt of the starting compound (VI) is used in this stage, the reaction is carried out in the presence of a base such as sodium hydroxide, potassium hydroxide, pyridine, trimethylamine, triethylamine or 4-dimethylaminopyridine.

Preparation method 4:

The benzothiazolinone derivative (Id) and its salt can be prepared by reacting the starting compound (II) with the starting compound (VII) or its reactive derivative.

Examples of the reactive derivatives of the starting materials (VII) include acid halides, acid active esters, acid anhydride and the like.

This reaction can be generally carried out in the presence of a base such as sodium hydroxide, potassium hydroxide, pyridine, trimethylamine, triethylamine or 4-dimethylaminopyridine, in a solvent such as tetrahydrofuran, dioxane or N,N-dimethylformamide with warming or heating.

The object compounds obtained by the above methods can be isolated and purified in a conventional manner.

The benzothiazoline derivatives (Ia), (Ib), (Ic), and (Id) all are included in the object compounds (I). Consequently, the salts of the benzothiazolinone derivatives (I) as examplified above are applicable to the salts of the benzothiazolinone derivatives (Id).

The benzothiazolinone derivatives (I) and pharmaceutically acceptable salts thereof may be administered in the form of conventional pharmaceutical preparations suitable for oral or parenteral administration or topical application, such as capsules, granules, powders, tablets, ointments, syrups, injections, suppositories, aerosols, inhalants or eye drops. These pharmaceutical preparations may be prepared in a conventional method, using conventional additives for preparations.

Examples of the additives for preparations include carrieres such as sucrose, lactose, glucose, starch, D-mannitol, D-sorbitol, crystalline cellulose, hydroxypropyl starch, talc, sodium hydrogenphosphate and calcium carbonate; binders such as methylcellulose, ethylcellulose, hydroxypropyl cellulose, hydroxypropyl methylcellulose, polyvinyl pyrrolidone, methylmethacrylate-methacrylic acid copolymer, gelatin, gum arabic, sucrose and starch; disintegrating agents such as starch, carboxymethyl cellulose or its calcium salt, hydroxypropyl cellulose with lower degree of substitution, croscarmellose sodium A type (Ac-Di-Sol), hydroxypropyl starch, crystalline cellulose and sodium lauryl sulfate; lubricants such as magnesium stearate, calcium stearate, talc and hydrated silicon dioxide; corrigents such as citric acid, menthol, ammonium glycyrrhetinate, glycine and orange powders; preservatives such as sodium benzoate, sodium hydrogen sulfite, methyl p-oxybenzoate and propyl p-oxybenzoate; stabilizers such as citric acid, sodium citrate and acetic acid; suspending agents such as methyl cellulose, polyvinyl pyrrolidone, carboxymethyl cellulose or its calsium salt and crystalline cellulose; dispersing agents such as polysorbate 80, Emalgen 408 (surfactant) and Emasol 310 (surfactant); solvents such as water; and bases such as cocoa butter, polyethyleneglycol, witepsol, white petrolatum and carboxyvinyl polymer.

These additives can be suitably chosen depending on the nature of the preparations.

The administration dosages of the benzothiazolinone derivatives and salts thereof are varied considerably taken into account the age and symptom of the subject and the manner for administration. When administered by oral route, injection or inhalation, the most suitable dosage can be chosen from the range of 0.1 to 1000 mg/kg/day, preferably 0.25 to 200 mg/kg/day. When administered topically by ointment, inhalation, etc, the dosage is determined considerably taken into account absorption by the tissue of the active ingredient from the preparation. Examples of dosage units of tablets are 50, 100, 200 mg, etc.; injections in intravenous route 12.5, 25 mg, etc. and that in subcutaneous route or in intramuscle route 15, 30 mg, etc.; suppository about 500 mg; and ointment about 100 to 2000 mg.

In addition to the compounds which will be described in the following examples, interesting compounds of the invention may be listed as follows.

4-chloro-3-(4-ethoxycarbonyloxypiperidinocarbonylmethyl)benzothiazolin-2-one, 6-chloro-3-(4-ethoxycarbonyloxypiperidinocarbonylmethyl)benzothiazolin-2-one, 7-chloro-3-(4-ethoxycarbonyloxypiperidinocarbonylmethyl)benzothiazolin-2-one, 4-chloro-3-[4-(N-methylcarbamoyloxy)piperdinocarbonylmethyl]benzothiazolin-2-one, 6-chloro-3-[4-(N-methylcarbamoyloxy)-piperidinocarbonylmethyl]benzothiazolin-2-one, 7-chloro-3-[4-(N-methylcarbamoyloxy)-piperidinocarbonylmethyl]benzothiazolin-2-one, 4-chloro-3-[4-(N-ethylcarbamoyloxy)piperidinocarbonylmethyl]benzothiazolin-2-one, 6-chloro-3-[4-(N-ethylcarbamoyloxy)piperidinocarbonylmethyl]benzothiazolin-2-one, 7-chloro-3-[4-(N-ethylcarbamoyloxy)piperdinocarbonylmethyl]benzothiazolin-2-one, 4-chloro-3-(4-carbamoyloxypiperidinocarbonylmethyl)benzothiazolin-2-one, 6-chloro-3-(4-carbamoyloxypiperidinocarbonylmethyl)benzothiazolin-2-one, 7-chloro-3-(4-carbamoyloxypiperidinocarbonylmethyl)benzothiazolin-2-one, 4-chloro-3-[4-(N,N-dimethylcarbamoyloxy)-piperidinocarbonylmethyl]benzothiazolin-2-one, 6-chloro-3-[4-(N,N-dimethylcarbamoyloxy)-piperidinocarbonylmethyl]benzothiazolin-2-one, 7-chloro-3-[4-(N,N-dimethylcarbamoyloxy)-piperidinocarbonylmethyl]benzothiazolin-2-one, 3-[1-(4-chloro-2-oxobenzothiazolin-3-yl-acetyl)-piperidin-3-yl-oxycarbonyl]propionic acid, 3-[1-(6-chloro-2-oxobenzothiazolin-3-yl-acetyl)-piperidin-3-yl-oxycarbonyl]propionic acid, 3-[1-(7-chloro-2-oxobenzothiazolin-3yl-acetyl)piperidin-3-yl-oxycarbonyl]propionic acid, 3-[1-(4-chloro-2-oxobenzothiazolin-3-yl-acetyl)-piperidin-4-yl-oxycarbonyl]propionic acid, 3-[1-(6-chloro-2-oxobenzothiazolin-3-yl-acetyl)-piperidin-4-yl-oxycarbonyl]propionic acid, 3-[1-(7-chloro-2-oxobenzothiazolin-3-yl-acetyl)-piperidin-4-yl-oxycarbonyl]propionic acid, 3-[1-(4-chloro-2-oxobenzothiazolin-3-yl-acetyl)-piperidin-4-yl-oxycarbonyl]acrylic acid, 3-[1-(6-chloro-2-oxobenzothiazolin-3-yl-acetyl)-piperidin-4-yl-oxycarbonyl]acrylic acid and 3-[1-(7-chloro-2-oxobenzothiazolin-3-yl-acetyl)-piperidin-4-yl-oxycarbonyl]acrylic acid, and sodium or potassium salt thereof when carboxyl group is contained in the molecule of the above-mentioned compounds.

(Effect)

The antiallergic and anti-inflammatory activities of the benzothiazolinone derivative (I) of the invention are described below.

TEST EXAMPLE 1

Antagonism to passive cutaneous anaphylaxis (P.C.A.) in rat:

Test method

Antiserum was prepared by the following method. One mg of egg albumin emulsified in 0.5 ml of Diphtheria-Pertussis-Tetanus Combined Vaccine (Tanabe Seiyaku Company Ltd.) and 0.5 ml of Freund's incomplete adjuvant (Seikagaku-Kogyo Company Ltd.) was used as the rat reaginic antiserum antigen against egg albumin. The emulsion was given subcutaneously in a single dose of 1 ml divided equally (0.25 ml) to the four foot pads of male SLC Wistar-strain rats aged 7 weeks, each weighing 170 to 190 g. Blood samples were collected 12 days after injection and centrifuged at 3000 r.p.m. at 4 C. for 15 minutes. The antisera thus obtained were stored at −20° C.

Groups consisting of five SLC Wistar-strain rats weighing 150 to 170 g were used. The rat reaginic antiserum against egg albumin was used at a dilution 1:4. The animals were sensitized with 0.1 ml of the antiserum injected intracutaneously on the depilated backs of the rats. Fortyeight hours after the injection of the antiserum, 1 ml of the mixture of egg albumin (5 mg) and Evan's blue (5 mg) in physiological saline (1 ml) was injected intravenously to cause the P.C.A. reaction. Thirty minutes after the injection of the antigen, animals were sacrificed and the skin was removed. The blue spots which occured due to the P.C.A. reaction were measured their long and short diameters and the areas of the spots were found from the average of the values of the diameters. Each test compound was given orally with 16 mg/kg and intravenously with 4 mg/kg, 1 hour and 5 minutes before injection for P.C.A. reaction respectively. The reaction inhibitory ratio of the group administered the test compound was calculated from the ratio of the areas of the control group and the group administered the test compound. Test compounds are as follows.

Compound A: 3-[1-(5-chloro-2-oxobenzothiazolin-3-yl-acetyl)piperidin-4-yl-oxycarbonyl]propionic acid, Compound B: 5-chloro-3-(4-ethoxycarbonyloxypiperidinocarbonylmethyl)benzothiazolin-2-one, Compound C: 5-chloro-3-[4-(N-ethylcarbamoyloxy)-piperidinocarbonylmethyl]benzothiazolin-2-one, and Compound D: 5-chloro-3-[4-(N,N-dimethylcarbamoyloxy)piperidinocarbonylmethyl]benzothiazolin-2-one.

Test results

The results are shown by the following Table 1.

Table 1 [P.C.A. reaction inhibitory ratio of rat (%)]

| Test compound | Oral administration | Intraveneous administration |
|---|---|---|
| A | 50.9 | 42.2 |
| B | 50.7 | 44.2 |
| C | 45.1 | 41.6 |
| D | 40.3 | 47.8 |

TEST EXAMPLE 2

Antagonism to acute edema at sole of hind leg in rat:
Groups consisting of five SLC Wistar-strain rats weighing 150 to 170 g were used.

Each test compound was given orally with 200 mg/kg and intravenously with 64 mg/kg, 30 minutes and five minutes respectively before subcutaneous injection of a prophlogistic substance (1 ml of 1% λ-carrageenin solution) into the sole of one hind leg. A volume of the sole was measured with time. The edema ratio of sole edema was calculated in comparison between the volumes of the sole before and after injection of the prophlogistic substance. The inhibition ratio was calculated from the difference of the edema ratio between the substance administered group and the control group.

Test compounds

The compounds A and C in the test example 1 were used.

Results

The results are shown by the following Table 2.

Table 2 Inhibitory ratio (%) of sole edema in rat

| Administrating route | Oral | | | Intravenous | |
| --- | --- | --- | --- | --- | --- |
| Measuring time (hr.) | 1 | 2 | 3 | 1 | 2 |
| Compound A | 24.5 | 62.3 | 69.4 | 83.2 | 24.2 |
| Compound C | — | — | — | 64.9 | 52.9 |

As clear from the above test results, the benzothiazolinone derivatives (I) of the present invention have excellent antiallergic and anti-inflammatory properties.

The benzothiazolinone derivatives (I) and their salts of the present invention possess not only antiallergic and anti-inflammatory properties but also blood platelets clotting inhibiting property and are useful as drugs for treating various diseases, e.g., bronchial asthma, allergic coryza, inflammatory diseases, dermatic diseases such as urticaria, or diseases caused by thrombus formed in brain and heart. Further, the benzothiazolinone derivatives (Id) show good water solubility and can be conveniently used for preparing liquid preparations such as a collunarium or an injection.

(Examples)

This invention is illustrated in further detail by the following examples.

EXAMPLE 1

Preparation of 5-chloro-3-(4-ethoxycarbonyloxypiperidinocarbonylmethyl)benzothiazolin-2-one:

5-Chloro-3-(4-hydroxypiperidinocarbonylmethyl)-benzothiazolin-2-one (3.2 g) was dissolved in dry pyridine (15 ml) and the solution was cooled. After ethyl chlorocarbonate (1.5 g) was dropwise added to the solution, the resultant was stirred for 8 hours at 80° C. Pyridine was evaporated off under vacuum from the reaction mixture and the residue was recrystallized from a mixture of chloroform and ethanol to yield the title compound as colorless crystals (3.2 g). mp 196°-197° C.

Elemental analysis for $C_{17}H_{19}N_2O_5SCl$

Calcd (%) C; 51.19, H; 4.80, N; 7.02. Found (%) C; 50.89, H; 4.50, N; 7.05.

NMR(CDCl$_3$)
δ:
1.35(3H, t, J=7 Hz), 1.55–2.30(4H, bs), 3.20–3.95(5H, bs), 4.22(2H, q, J=7 Hz), 4.69(2H, s), 6.85–8.30(3H, m)

EXAMPLE 2

Preparation of 5-chloro-3-[4-(N-methylcarbamoyloxy)piperidinocarbonylmethyl]benzothiazolin-2-one:

5-Chloro-3-(4-hydroxypiperidinocarbonylmethyl)-benzothiazolin-2-one (3.2 g) was dissolved in dry pyridine (15 ml) and the solution was cooled. After methyl isocyanate (0.9 g) was dropwise added to the solution, the resultant was stirred for 15 hours at 30° C. Pyridine was evaporated off under vacuum from the reaction mixture and the residue was recrystallized from methanol to yield the title compound as colorless crystals (2.7 g). mp 202°-203° C.

Elemental analysis for $C_{16}H_{18}N_3O_4SCl$

Calcd (%) C; 50.07, H; 4.73, N; 10.95. Found (%) C; 49,98, H; 4,50, N; 10.99.

NMR(CDCl$_3$)
δ:
1.50–2.20(4H, bs), 2.75(3H, d, J=5 Hz), 3.10–3.90(5H, bs), 4.60(2H, s), 6.70–7.15 (4H, m)

EXAMPLE 3

Preparation of 5-chloro-3[4-(N-ethylcarbamoyloxy)-piperidinocarbonylmethyl]benzothiazolin-2-one: 5-Chloro-3-(4-hydroxypiperidinocarbonylmethyl)benzothiazolin-2-one (3.2 g) was dissolved in dry pyridine (15 ml) and the solution was cooled. After ethyl isocyanate (0.9 g) was dropwise added to the solution, the resultant was stirred for 10 hours at 50° C. Pyridine was evaporated off under vacuum from the reaction mixture and the residue was recrystallized from ethanol to yield the title compound as colorless crystals (3.0 g). mp 210°-211° C.

Elemental analysis for $C_{17}H_{20}N_3O_4SCl$

Calcd. (%) C; 51.32, H; 5.07, N; 10.56. Found (%) C; 51.11, H; 4.74, N; 10.58.

NMR(CDCl$_3$)
δ:
1.15(3H, t, J-7 Hz), 1.50–2.20(4H, bs), 3.00–4.00(7H, bs), 4.65(2H, s), 6.80–7.25(4H, m)

EXAMPLE 4

Preparation of 5-chloro-3-(4-carbamoyloxypiperidinocarbonylmethyl)benzothiazolin-2-one:

A solution of 5-chloro-3-(4-hydroxypiperidinocarbonylmethyl)benzothiazolin-2-one (3.2 g) in dry dioxane (70 ml) was gradually dropped in a phosgene solution in dry dioxane (10 ml), under cooling. The mixture was left for two hours at room temperature. After cooling, to the mixture was gradually dropwise added 28% aqueous ammonia (5 ml) and the resultant was stirred for two hours at room temperature. Dioxane was evaporated off under vacuum from the reaction mixture. The residue was washed with water and then recrystallized from a mixture of dioxane and ethanol to yield the title compound as colorless crystals (2.8 g). m.p. 210°-212° C.

Elemental analysis for $C_{15}H_{16}N_3O_4SCl$

Calcd. (%) C; 48.72, H; 4.36, N; 11.36. Found (%) C; 48.51, H; 4.23, N; 11.39.

NMR(DMSO-d$_6$)
δ:
1.10–2.30(4H, bs), 2.80–4.20(5H, bs), 4.97(2H, s), 6.49(2H, s), 7.00–7.90(3H, m)

EXAMPLE 5

Preparation of 5-chloro-3-[4-(N,N-dimethyl carbamoyloxy)piperdinocarbonylmethyl]benzothizolin-2-one:

A solution of 5-chloro-3-[4-hydroxypiperidinocarbonylmethyl]benzothiazolin-2-one (3.2 g) in dry tetrahydrofuran (60 ml) was cooled, to which a solution of trichloromethylchloroformate (0.61 ml) in dry tetrahydrofuran (2 ml) and a solution of triethylamine (1.4 ml) in dry tetrahydrofuran (4 ml) were dropwise added. After stirring for two hours at 60° C., the mixture was left overnight. After cooling the mixture, 50% aqueous dimethylamine (1.5 ml) was dropwise added to the mixture under stirring, followed by stirring for two hours at room temperature. Tetrahydrofuran was evaporated off under vacuum from the reaction mixture, and the residue was washed with water and then recrystallized from methanol to yield the title compound as colorless crystals (2.1 g). m.p. 148°–150° C.

Elemental analysis for $C_{17}H_{20}N_3O_4SCl$

Calcd. C; 51.32, H; 5.07, H; 10.56. Found: C; 51.11, H; 4.88, N; 10.68.

NMR(CDCl$_3$)
δ:
1.50–2.20(4H, bs), 2.90(6H, s), 3.20–4.00 (4H, bs), 4.66(2H, s), 4.75–5.10(1H, bs), 6.80–7.40(3H, m)

EXAMPLE 6

Preparation of 3-[1-(5-chloro-2-oxobenzothiazolin-3-yl-acetyl)piperidin-3-yl-oxycarbonyl]propionic acid:

A solution of 5-chloro-3-(3-hydroxypiperidinocarbonylmethyl)benzothiazolin-2-one (3.2 g) in dry pyridine (2.5 ml) and dry tetrahydrofuran (50 ml) was cooled. To the solution was dropwise added a solution of succinic anhydride (1.1 g) in dry tetrahydrofuran (5 ml) under stirring. The mixture was refluxed for two hours and then left overnight. The solvent was evaporated off under vacuum from the reaction mixture. The residue was dissolved in 5% aqueous sodium bicarbonate (20 ml). The resultant solution was cooled and adjusted to pH 2 with 1% hydrochloric acid. The precipitated crystals were collected by filtration, washed with water and then recrystallized from isopropyl alcohol to yield the title compound as colorless crystals (2.0 g). m.p. 131°–133° C.

Elemental analysis for $C_{18}H_{19}N_2O_6SCl$

Calcd. C; 50.65, H; 4.49, N; 6.56, Found: C; 50.39, H; 4.25, N; 6.77.

NMR(DMSO-d$_6$)
δ:
1.40–2.20(4H, bs), 2.62(4H, s), 3.00–4.50(5H, bs), 4.95(2H, s), 6.90–7.90(3H, m), 11.90(1H, bs)

The above compound (1.0 g) was dissolved in a solution of sodium bicarbonate (0.2 g) in water (10 ml) and water was distilled off under vacuum at below 50° C. to yield sodium salt of the title compound as colorless crystals.

NMR(DMSO-d$_6$)
δ:
1.40–2.20(4H, bs), 2.60(4H, s), 3.00–4.50(5H, bs), 4.93(2H, s), 6.90–7.90(3H, m)

EXAMPLE 7

Preparation of 3-[1-(5-chloro-2-oxobenzothiazolin-3-yl-acetyl)piperidin-4-yl-oxycarbonyl]propionic acid:

A solution of 5-chloro-3-(4-hydroxypiperidinocarbonylmethyl)benzothiazolin-2-one (3.2 g) in dry pyridine (2.5 ml) and dry tetrahydrofuran (50 ml) was cooled. To the solution was dropwise added a solution of succinic anhydride (1.1 g) in dry tetrahydrofuran (5 ml) under stirring. The mixture was refluxed for 2 hours and then left overnight. The reaction mixture was treated in the same manner as that in Example 6 to yield the title compound as colorless crystals (2.5 g).

m.p. 154°–156° C.

Elemental analysis for $C_{18}H_{19}N_2O_6SCl$

Calcd. (%) C; 50.65, H; 4.49, N; 6.56. Found (%) C; 50.54, H; 4.37, N; 6.53.

NMR(DMSO-d$_6$)
δ:
1.25–2.20(4H, bs), 2.53(4H, s), 3.10–4.00(5H, bs), 4.96(2H, s), 7.15–7.85(3H, m), 11.90(1H, bs)

The above compound was treated with sodium bicarbonate in the same manner as that in Example 6 to yield sodium salt of the title compound as colorless crystals.

NMR(DMSO-d$_6$)
δ:
1.25–2.20(4H, bs), 2.50(4H, s), 3.10–4.00(5H, bs), 4.92(2H, s), 7.15–7.85(3H, m)

EXAMPLE 8

Preparation of 3-[1-(5-chloro-2-oxobenzothiazolin-3-yl-acetyl)piperidin-4-yl-oxycarbonyl]acrylic acid:

A solution of 5-chloro-3-(4-hydroxypiperidinocarbonylmetyl)benzothiazolin-2-one (3.2 g) in dry pyridine (2.5 ml) and dry tetrahydrofuran (50 ml) was cooled, to which a solution of maleic anhydride (1.0 g) in dry tetrahydrofuran (5 ml) was gradually dropwise added under stirring. The mixture was refluxed for two hours and then left overnight. The solvent was evaporated off under vacuum from the reaction mixture, and the residue was dissolved in 5% aqueous sodium bicarbonate (20 ml). The solution was cooled and adjusted to pH 2 with 1% hydrochloric acid. The precipitated crystals were collected by filtration, washed with water and then subjected to chromatography on silica gel eluting with ethanol/benzene (1:1). The solvent was evaporated off under vacuum from the eluate at below 50° C. The residue was recrystallized from isopropyl alcohol to yield the title compound as colorless crystals (2.1 g). m.p. 197°–198° C.

Elemental analysis for $C_{18}H_{17}N_2O_6SCl$

Calcd. (%) C; 50.89, H; 4.03, N; 6.59. Found: (%) C; 50.63, H; 4.21, N; 6.72.

NMR(DMSO-d$_6$)
δ:
1.50–2.30(4H, bs), 3.10–4.10(5H, bs), 4.95(2H, s), 5.87(1H, d, J=12 Hz), 6.55 (1H, d, J=12 Hz), 7.10–7.80(3H, m), 11.90(1H, bs)

The above compound was treated with sodium bicarbonate in the same manner as that in Example 6 to yield sodium salt of the title compound as colorless crystals.

NMR(DMSO-d$_6$)
δ:
1.50–2.30(4H, bs), 3.10–4.10(5H, bs), 4.97(2H, s), 5.89(1H, d, J=12 Hz), 6.57(1H, d, J=12 Hz), 7.10–7.80(3H, m)

EXAMPLE 9

| | | |
|---|---|---|
| 3-[1-(5-chloro-2-oxobenzo thiazolin-3-yl-acetyl)piperidin-4-yl-oxycarbonyl]propionic acid (referred to as Compound A hereafter) | 500 | (parts by weight) |
| Lactose | 9250 | " |

-continued

| | | |
|---|---|---|
| Hydroxypropyl cellulose | 200 | " |
| Strach | 50 | " |

The above ingredients were blended and granulated in a conventional manner into granules.

EXAMPLE 10

| | | |
|---|---|---|
| 5-Chloro-3-[4-(N,N—dimethyl carbamoyloxy)piperidinocarbonyl methyl]benzothiazolin-2-one (referred to as Compound D hereafter) | 500 | (parts by weight) |
| Lactose | 8500 | " |
| Hydroxypropyl cellulose | 200 | " |
| Strach | 500 | " |
| Crystalline cellulose | 300 | " |

The above ingredients were blended and granulated in a conventional manner into small grains.

EXAMPLE 11

| | | |
|---|---|---|
| Compound A | 500 | (parts by weight) |
| D-mannitol | 1987 | " |
| Magnesium stearate | 3 | " |

The above ingredients were blended and filled in hard gelatin-capsules, in a conventional manner, to give capsules, each of which contains 50 mg of Compound A.

EXAMPLE 12

| | | |
|---|---|---|
| Compound A | 500 | (parts by weight) |
| Sucrose | 9250 | " |
| Citric acid | 20 | " |
| Hydroxypropyl cellulose | 200 | " |
| Sodium benzoate | 50 | " |

The above ingredients was blended in a conventional manner to make a dry-syrup.

EXAMPLE 13

| | | |
|---|---|---|
| 5-Chloro-3-[4-(N—ethylcarbamoyloxy)piperidinocarbonylmethyl] benzothiazolin-2-one (referred to as Compound C hereafter) | 10000 | (parts by weight) |
| Lactose | 3000 | " |
| Croscarmellose sodium A type (Ac—Di-Sol) | 3000 | " |
| Hydroxypropyl cellulose | 1800 | " |
| Magnesium stearate | 200 | " |

The above ingredients were blended and compressed, in a conventional manner, into tablets, each of which contains 100 mg of Compound C.

EXAMPLE 14

| | | |
|---|---|---|
| Compound A | 20000 | (parts by weight) |
| Lactose | 10400 | " |
| Hydroxypropyl cellulose with lower degree of substitution | | |
| Hydroxypropyl cellulose | 1800 | " |
| Magnesium stearate | 200 | " |

The above ingredients were blended and compressed, in a conventional manner, into tablets, each of which contains 200 mg of Compound A and then the tablets were coated with film-coating, in a conventional manner, to give film-coated tablets.

EXAMPLE 15

| | | |
|---|---|---|
| 5-Chloro-3-(4-ethoxycarbonyloxy piperidinocarbonylmethyl) benzothiazolin-2-one (referred to as Compound B) | 5000 | (parts by weight) |
| Lactose | 4200 | " |
| Hydroxypropyl cellulose with lower degree of substitution | 1100 | " |
| Hydroxypropyl cellulose | 600 | " |
| Magnesium stearate | 100 | " |

The above ingredients were blended and compressed, in a conventional manner, into tablets, each of which contains 50 mg of Compound B, and then the tablets were subjected to sugar-coating.

EXAMPLE 16

| | | |
|---|---|---|
| Compound A | 25000 | (parts by weight) |
| Lactose | 14600 | " |
| Crystalline cellulose | 4700 | " |
| Ethyl cellulose | 600 | " |
| Hydroxypropyl cellulose | 1800 | " |
| Magnesium stearate | 100 | " |

The above ingredients were blended and granuled, in a conventional manner, into fast-soluble granules and sustained release granules.

These granules were compressed into tablets, each containing 250 mg of Compound A, and the tablets were subjected to film-coating in a conventional manner, to give film-coated sustained release tablets.

EXAMPLE 17

| | | |
|---|---|---|
| Compound A | 1000 | (parts by weight) |
| Sodium bicarbonate | 84 | " |
| Citric acid | 20 | " |
| Methyl p-oxybenzoate | 25 | " |
| Propyl p-oxybenzoate | 15 | " |
| Sucrose | 4500 | " |

The above ingredients were dissolved in purified water to make a syrup of which total amount is 10,000 parts by weight.

EXAMPLE 18

| | | |
|---|---|---|
| Compound D | 1000 | (parts by weight) |
| Citric acid | 10 | " |
| Crystalline cellulose | 800 | " |
| Methyl p-oxybenzoate | 25 | " |
| Propyl p-oxybenzoate | 15 | " |
| Sucrose | 4500 | " |

The above ingredients were suspended or dissolved in purified water to make a syrup of which total amount is 10,000 part by weight.

EXAMPLE 19

| | | |
|---|---|---|
| Compound A | 2500 | (parts by weight) |
| Sodium hydroxide | 40 | " |

| -continued |  |  |
|---|---|---|
| Methyl p-oxybenzoate | 10 | " |
| Polysorbate 80 | 10 | " |
| Lidocaine hydrochloride | 50 | " |

The above ingredients were dissolved in distilled water for injection to make injectable solution of which total amount is 10,000 parts by weight.

EXAMPLE 20

| Compound A | 500 | (parts by weight) |
|---|---|---|
| White petrolatum | 9025 | " |
| Sorbitan trioleate | 475 | " |

The above ingredients were blended and kneaded into ointment.

EXAMPLE 21

| Compound A | 5000 | (parts by weight) |
|---|---|---|
| White petrolatum | 40000 | " |
| Sorbitan sesquioleate | 5000 | " |
| Cetanol | 18000 | " |
| Lauromacrogol | 500 | " |
| Butyl p-oxylenzoate | 100 | " |

The above ingredients were blended and kneaded into ointment.

EXAMPLE 22

| Compound A | 250 | (parts by weight) |
|---|---|---|
| Lactic acid | 250 | " |

The above ingredients were blended and filled in capsules to give capsules, for inhalation, each of which contains 25 mg of Compound A.

EXAMPLE 23

| Compound A | 100 | (parts by weight) |
|---|---|---|
| Sodium bicarbonate | 10 | " |
| Polysorbate 80 | 40 | " |
| Methyl p-oxybenzoate | 26 | " |
| Propyl p-oxybenzoate | 14 | " |

The above ingredients were dissolved in sterile purified water to make eyedrop of which total amount is 10,000 parts by weight.

What we claim is:

1. A benzothiazolinone derivative of the formula

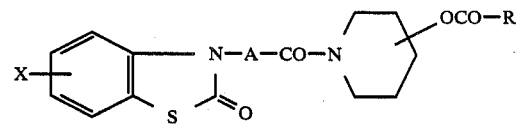

in which A is a lower alkylene group, X is a halogen atom, and R is $-CH_2CH_2COOH$ or $-CH=CH-COOH$; or a pharmaceutically acceptable salt thereof.

2. 3-[1-(5-chloro-2-oxo-benzothiazolin-3-ylacetyl)-piperidin-3-yloxycarbonyl]propionic acid or the sodium salt thereof.

3. An anti-allergic or anti-inflammatory composition comprising a carrier and an anti-allergic- or anti-inflammatory-effective amount of the benzothiazolinone derivative or salt of claim 1.

4. An anti-allergic or anti-inflammatory composition comprising a carrier and an anti-allergic- or anti-inflammatory-effect amount of the benzothiazolinone derivative or salt of claim 2.

* * * * *